US008758357B2

(12) United States Patent
Frey

(10) Patent No.: US 8,758,357 B2
(45) Date of Patent: Jun. 24, 2014

(54) PATIENT MATCHING SURGICAL GUIDE AND METHOD FOR USING THE SAME

(76) Inventor: George Frey, Englewood, CO (US)

(*) Notice: Subject to any disclaimer, the term of this patent is extended or adjusted under 35 U.S.C. 154(b) by 369 days.

(21) Appl. No.: 13/172,683

(22) Filed: Jun. 29, 2011

(65) Prior Publication Data

US 2011/0319745 A1 Dec. 29, 2011

Related U.S. Application Data

(60) Provisional application No. 61/359,710, filed on Jun. 29, 2010, provisional application No. 61/393,695, filed on Oct. 15, 2010.

(51) Int. Cl.
*A61B 17/58* (2006.01)
(52) U.S. Cl.
USPC ............................................. 606/96; 600/424
(58) Field of Classification Search
USPC ........ 600/407–430, 437–469; 606/79, 88–96; 602/26
See application file for complete search history.

(56) References Cited

U.S. PATENT DOCUMENTS

| 5,201,734 | A | 4/1993 | Cozad et al. |
| D359,557 | S | 6/1995 | Hayes |
| D403,066 | S | 12/1998 | DeFonzo |
| D412,032 | S | 7/1999 | Mikula-Curtis et al. |
| D420,132 | S | 2/2000 | Bucholz et al. |
| D428,989 | S | 8/2000 | Segermark et al. |
| 6,711,432 | B1 * | 3/2004 | Krause et al. ................. 600/427 |
| 6,755,839 | B2 | 6/2004 | Van Hoeck et al. |
| D532,515 | S | 11/2006 | Buttler et al. |
| D533,664 | S | 12/2006 | Buttler et al. |
| 7,658,610 | B2 | 2/2010 | Knopp |
| D618,796 | S | 6/2010 | Cantu et al. |
| 7,844,356 | B2 | 11/2010 | Matov et al. |
| 7,957,824 | B2 | 6/2011 | Boronvinskih et al. |

(Continued)

FOREIGN PATENT DOCUMENTS

| CN | 201275138 | 7/2009 |
| CN | 201404283 | 2/2010 |

(Continued)

OTHER PUBLICATIONS

Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract Only).

(Continued)

*Primary Examiner* — Sanjay Cattungal
(74) *Attorney, Agent, or Firm* — Sheridan Ross P.C.

(57) ABSTRACT

A system and method for developing customized apparatus for use in one or more surgical procedures is disclosed. The system and method incorporates a patient's unique anatomical features or morphology, which may be derived from capturing MRI data or CT data, to fabricate at least one custom apparatus. According to a preferred embodiment, the customized apparatus comprises a plurality of complementary surfaces based on a plurality of data points from the MRI or CT data. Thus, each apparatus may be matched in duplicate and oriented around the patient's own anatomy, and may further provide any desired axial alignments or insertional trajectories. In an alternate embodiment, the apparatus may further be aligned with at least one other apparatus used during the surgical procedure.

20 Claims, 15 Drawing Sheets

(56) References Cited

U.S. PATENT DOCUMENTS

| | | | |
|---|---|---|---|
| 8,206,396 B2 * | 6/2012 | Trabish | 606/89 |
| 8,257,083 B2 * | 9/2012 | Berckmans et al. | 433/213 |
| D669,176 S | 10/2012 | Frey | |
| D672,038 S | 12/2012 | Frey | |
| 8,357,111 B2 * | 1/2013 | Caillouette et al. | 602/26 |
| 8,419,740 B2 * | 4/2013 | Aram et al. | 606/88 |
| 2004/0097925 A1 | 5/2004 | Boehm et al. | |
| 2006/0084986 A1 | 4/2006 | Grinberg et al. | |
| 2007/0288030 A1 | 12/2007 | Metzger et al. | |
| 2008/0114370 A1 * | 5/2008 | Schoenefeld | 606/96 |
| 2008/0161815 A1 | 7/2008 | Schoenefeld et al. | |
| 2008/0183214 A1 | 7/2008 | Copp et al. | |
| 2008/0257363 A1 | 10/2008 | Schoenefeld et al. | |
| 2008/0275452 A1 | 11/2008 | Lang et al. | |
| 2008/0312659 A1 | 12/2008 | Metzger et al. | |
| 2008/0319491 A1 | 12/2008 | Schoenefeld | |
| 2009/0087276 A1 | 4/2009 | Rose | |
| 2009/0088674 A1 * | 4/2009 | Caillouette et al. | 602/26 |
| 2009/0088761 A1 * | 4/2009 | Roose et al. | 606/87 |
| 2009/0088763 A1 * | 4/2009 | Aram et al. | 606/88 |
| 2009/0093816 A1 * | 4/2009 | Roose et al. | 606/87 |
| 2009/0099567 A1 * | 4/2009 | Zajac | 606/79 |
| 2009/0110498 A1 | 4/2009 | Park | |
| 2009/0138020 A1 | 5/2009 | Park et al. | |
| 2009/0187194 A1 | 7/2009 | Hamada | |
| 2009/0198277 A1 | 8/2009 | Gordon et al. | |
| 2009/0254093 A1 | 10/2009 | White et al. | |
| 2009/0270868 A1 | 10/2009 | Park et al. | |
| 2010/0049195 A1 | 2/2010 | Park et al. | |
| 2010/0087829 A1 | 4/2010 | Metzger et al. | |
| 2010/0100193 A1 | 4/2010 | White | |
| 2010/0152782 A1 | 6/2010 | Stone et al. | |
| 2010/0191244 A1 | 7/2010 | White et al. | |
| 2010/0217270 A1 | 8/2010 | Polinski et al. | |
| 2010/0217336 A1 | 8/2010 | Crawford et al. | |
| 2010/0305700 A1 | 12/2010 | Ben-Arye et al. | |
| 2010/0324692 A1 | 12/2010 | Uthgenannt et al. | |
| 2011/0015636 A1 | 1/2011 | Katrana et al. | |
| 2011/0015639 A1 | 1/2011 | Metzger et al. | |
| 2011/0046735 A1 | 2/2011 | Metzger et al. | |
| 2011/0054478 A1 | 3/2011 | Vanasse et al. | |
| 2011/0071533 A1 | 3/2011 | Metzger et al. | |
| 2011/0093023 A1 | 4/2011 | Lee et al. | |
| 2011/0093086 A1 | 4/2011 | Witt et al. | |
| 2011/0160736 A1 | 6/2011 | Meridew et al. | |
| 2011/0160867 A1 | 6/2011 | Meridew et al. | |
| 2011/0166578 A1 | 7/2011 | Stone et al. | |
| 2011/0184419 A1 | 7/2011 | Meridew et al. | |
| 2011/0184526 A1 | 7/2011 | White et al. | |
| 2011/0190899 A1 | 8/2011 | Pierce et al. | |
| 2011/0213376 A1 | 9/2011 | Maxson et al. | |
| 2011/0218545 A1 | 9/2011 | Catanzarite et al. | |
| 2011/0224674 A1 | 9/2011 | White et al. | |
| 2011/0288433 A1 | 11/2011 | Kelleher et al. | |
| 2011/0319745 A1 * | 12/2011 | Frey | 600/407 |
| 2012/0041445 A1 * | 2/2012 | Roose et al. | 606/96 |
| 2012/0130434 A1 | 5/2012 | Stemniski | |
| 2012/0215315 A1 | 8/2012 | Hochschuler et al. | |

FOREIGN PATENT DOCUMENTS

| | | |
|---|---|---|
| CN | 101390773 | 11/2010 |
| CN | 101953713 | 1/2011 |
| WO | WO 2007/145937 | 12/2007 |
| WO | WO 2008/027549 | 3/2008 |
| WO | WO 2009/129063 | 10/2009 |
| WO | WO 2010/148103 | 12/2010 |
| WO | WO 2011/041398 | 4/2011 |
| WO | WO 2011/080260 | 7/2011 |
| WO | WO 2011/106711 | 9/2011 |
| WO | WO 2011/109260 | 9/2011 |

OTHER PUBLICATIONS

Lu et al. "A Novel Patient-Specific Navigational Template for Cervical Pedicle Screw Placement," Spine, Dec. 15, 2009, vol. 34, No. 26, pp. E959-E966 (Abstract Only).

Owen et al. "Rapid prototype patient-specific drill template for cervical pedicle screw placement." Computer Aided Surgery, Sep. 2007, vol. 12, No. 5, pp. 303-308 (Abstract Only).

Ryken et al. "Image-based drill templates for cervical pedicle screw placement Laboratory investigation," Journal of Neurosurgery, Jan. 2009, vol. 10, No. 1 (Abstract Only).

Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).

International Search Report and Written Opinion for International (PCT) Patent Application No. PCT/US11/42412 mailed Nov. 8, 2011, 8 pages.

International Preliminary Report on Patentability for International (PCT) Patent Application No. PCT/US11/42412 mailed Jan. 17, 2013, 7 pages.

U.S. Appl. No. 29/432,668, filed Sep. 18, 2012, Frey.

Notice of Allowance for U.S. Appl. No. 29/409,734, mailed May 11, 2012 8 pages.

Notice of Allowance for U.S. Appl. No. 29/427,918, mailed Oct. 15, 2012 9 pages.

International Search Report and Written Opinion for International (PCT) Patent Application No. PCT/US2013/036535, mailed Jun. 26, 2013 8 pages.

* cited by examiner

PATIENT MATCHING SURGICAL GUIDE AND METHOD FOR USING THE SAME

CROSS-REFERENCE TO RELATED APPLICATIONS

The present application claims priority from U.S. Provisional Application Nos. 61/359,710, filed Jun. 29, 2010 and 61/393,695, filed Oct. 15, 2010, the entire disclosures of which are hereby incorporated by reference.

FIELD OF THE INVENTION

The present disclosure relates to the field of medical devices and is generally directed toward apparatus configurable for use with a specific patient in a surgical setting based on the patient's unique anatomical features, and methods of manufacturing and using the same.

BACKGROUND OF THE INVENTION

Given the complexities of surgical procedures and the various tools, instruments, implants and other devices used in the procedures, as well as the varying anatomical differentiation between patients who receive those tools, instruments, implants and devices, it is often challenging to create a surgery plan that accounts for the unique and sometimes irregular anatomical features of a particular patient. For example, the implantation of pedicle screws in a vertebral body (as a adjunct or stand-alone stabilization mechanism) is well accepted amongst surgeons who treat various spine pathologies, and although the performance of various pedicle screw constructs have become predictable, there are still multiple challenges with the placement and insertion of the pedicle screws or other bone anchors. The challenges occur when a surgeon is unable to reference bony landmarks due to previous surgery or when the patient's anatomy is irregular in shape.

As a result of these challenges, efforts have been made to develop technologies that assist the surgeon with the insertion, placement and/or alignment of individual instruments and/or implants that rely on pre-operative planning in conjunction with real time image-guided systems. One such system is disclosed in WIPO Publication No. WO 2008027549 to Crawford et al., which includes use of modeling anatomical features of a patient in conjunction with a haptic interface to simulate a surgical procedure in a pre-operative setting. Although systems like the one disclosed by Crawford et al. offer visual assistance with the placement of instruments and implants, the simulations are time-consuming and impractical for a number of surgical procedures. Furthermore, these systems rely on technologies that have not been widely accepted due in part to the cost of the technologies, and provide several intra-operative challenges, such as overreliance on engineering for fabricating each anatomical model and analytical analysis of those models, which most surgeons wish to avoid.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a custom implant based on the dynamic nature of the anatomical structures the custom implant is designed to associate with. This data, while currently used by surgeons in surgery planning, is largely unused for creating a customized set of instruments or other surgical devices that are designed to complement the patient's unique anatomy. Others have used this data to create, for example, a user-defined surgical guide for making an incision in the desired location, as is disclosed in U.S. Publication No. 20080114370 to Schoenefeld. However, Schoenefeld discloses a surgical guide that only partially penetrates the subcutaneous portion of the patient's anatomy (i.e., only a small portion of the guide is inserted through the incision, while the main body of the guide remains external to the incision). Furthermore, the guide disclosed in Schoenefeld uses only a limited number of unique data points to match the guide with the patient's anatomy, and thus may easily become misaligned or improperly oriented during the surgical procedure. Schoenefeld also fails to disclose customized apparatus manufactured by rapid prototyping equipment that not only matches an anatomical feature of the patient, but also matches one or more other apparatus used in the surgical procedure, such as a customized tool or instrument or one additional surgical guide, for example.

The prior art also fails to teach a system for creating a suite of surgical apparatus based on the data set derived from the MRI or CT scan. For example, the use of the patient specific data set for a vertebral body may allow a surgeon to accommodate for subtle variations in the position and orientation of plate to avoid particular bony anatomy or irregularities in the positioning and alignment of the adjoining vertebral bodies. As another example, the use of these data sets may also assist a surgeon in selecting a desired trajectory for an implantable device so as to avoid, for example, crossing the pedicle wall and violating the spinal canal during an actual procedure. The use of the data sets permit the surgeon to avoid these types of mistakes by creating customized tools and instruments, which may comprise end-stops or other safety related features to avoid over-torque and over-insertion of any implantable devices. The data sets also permit the surgeon to create a patient-contacting surface that is oriented to match one or more of the anatomical features represented by the data set, and thereby quickly and efficiently locate and place the patient-contacting surface(s) in the appropriate location and orientation.

It would therefore be advantageous to provide apparatus suitable for use with a surgical procedure that is adapted and/or configured and/or capable of conforming to a plurality of anatomical features of a particular patient and/or to one or more additional apparatus to assist the surgeon in completing the surgical procedure(s) safely and efficiently, and that otherwise significantly reduces, if not eliminates, the problems and risks noted above. Other advantages over the prior art will become known upon review of the Summary and Detailed Description of the Invention and the appended claims.

SUMMARY OF THE INVENTION

According to one aspect of the present disclosure, a novel system and method is described for developing customized apparatus for use in one or more surgical procedures. The system and method according to this embodiment uses a patient's unique morphology, which may be derived from capturing MRI data or CT data to derive one or more "Patient Matched" apparatus, which comprises complementary surfaces based on a plurality of data points from the MRI or CT data. Each "Patient Matched" apparatus is matched and oriented around the patient's own anatomy, the desired insertional trajectories (which may be verified in a pre-operative setting using 3D CAD software, such as the software disclosed in WO 2008027549, which is incorporated by reference herein in its entirety), and according to one embodiment described herein, other apparatus used during the surgical procedure.

The customized and integrated matching aspects of this presently disclosed system provides an advantage over the prior art, in particular by providing a plurality of interlocking and/or matching points for each apparatus, which in turn reduces the likelihood of misalignment, misplacement and subsequent mistake during the surgical procedure(s).

According to one aspect of the present disclosure, a system and method for facilitating a surgical procedure(s) comprises the following steps:

Obtaining data associated with the patient's anatomy by way of a MRI or CT scan;

Converting the MRI or CT scan data to a 3-Dimensional data set(s)

Determining one or more axes of orientation of a device to be constructed for use in facilitating the surgical procedure(s) to be performed on the patient;

Modeling the device for use in facilitating the surgical procedure(s) using the determined axes and accounting for any other constraints derived from the converted data set(s);

Generating a prototype of the modeled device by, for example, use of rapid prototyping machinery; and Preparing the prototype for use during the surgical procedure(s).

According to this aspect described above, the method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc.

According to yet another aspect of the present disclosure, the system and method includes use of data obtained from an ultrasonic or nuclear medicine scanning device.

In yet another alternative embodiment, the data obtained from one of the scanning devices described above may be supplemented or merged with data from a bone density scanner to fabricate a device that is designed to remain in the patient after the surgical procedure is completed. Examples of devices that remain in the patient include anchoring devices and implantable devices.

According to yet another embodiment, the data obtained from the patient permits the apparatus to be manufactured with defined pathways through the apparatus, which are operatively associated with at least one tool, instrument, or implant, and which permit the at least one tool, instrument or implant to be inserted in the defined pathways in a consistent and reproducible manner.

According to yet another aspect of the present disclosure, data may be supplemented or merged with data from a bone density scanner to achieve further control over the orientation of any desired axes, particularly where the surgical procedure involves insertion of one or more implantable devices.

According to yet another aspect of the present disclosure, a preconfigured surgical template is disclosed, which comprises one or more guides for receiving at least one tool. According to this embodiment, the one or more guides further comprise patient-contacting surfaces formed to be substantially congruent with the anatomical features of a patient. The preconfigured surgical template is configured such that the patient-contacting surfaces are configured to contact the plurality of anatomical features in a mating engagement, to ensure proper alignment and mounting of the guide or template, and the guides of the preconfigured surgical template are oriented in a direction selected prior to manufacturing of the preconfigured surgical template to achieve desired positioning, aligning or advancing of a tool within the one or more guides.

According to yet another aspect of the present disclosure, a method for creating a template for use in a surgical operation is disclosed, comprising the steps of:

collecting data from the patient corresponding to the patient's unique anatomy;

creating a model of the template from the data collected, the model comprising a plurality of matching surfaces to the patient's unique anatomy;

providing data associated with model to fabrication machinery;

rapidly generating the template to comprise the plurality of matching surfaces and further comprising at least one additional matching surface corresponding to at least one tool or instrument used in the surgical operation; and generating a permanent device based on the template for use in the surgical operation.

In one embodiment of the present disclosure the model is a digital model. In another embodiment of the present disclosure the model is a physical model.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356 and 7,658,610, and U.S. Pat. Pub. Nos. 20100217336, 20090138020, 20090087276 and 20080114370.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

Embodiments of the present disclosure present several advantages over the prior art including, for example, the speed and efficacy of the procedure, the minimally invasive aspects of the procedure, the disposability of the prototype devices, the ability to introduce customized implements or tools to the surgical site with minimal risk and damage to the surrounding tissue, lower risk of infection, more optimally placed and/or oriented guides and implantable devices, a more stable and controlled method of placing and inserting of apparatus associated with the surgical procedure further reducing the likelihood of the apparatus becoming misaligned or dislodged, and fewer and/or less expensive tools and instruments in a surgical site, among other advantages.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, resins, particularly fiber-encased resinous materials rubber, latex, synthetic rubber, synthetic materials, polymers, and natural materials.

One having skill in the art will appreciate that embodiments of the present disclosure may be used in conjunction devices that employ automated or semi-automated manipulation. Embodiments of the present disclosure may be designed such that the apparatus may be formed and verified, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. It is expressly understood for purposes of this disclosure that other types of machinery other than rapid prototyping machinery may be employed in the systems and methods described herein, for example, by computerized numerical control (CNC) machinery.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

In the drawings:

FIG. 1 is a perspective view of a three-dimensional model of a unique grouping of anatomical features from which a set of data points may be derived according to one embodiment of the present disclosure;

FIG. 2 is a flow chart diagram showing the various steps of performing a method of manufacturing and using an apparatus for facilitating a surgical procedure according to one embodiment of the present disclosure;

FIG. 3 is a side elevation view of a particular apparatus for facilitating a surgical procedure according to one embodiment of the present disclosure;

FIG. 4 is rear elevation view of the apparatus shown in FIG. 3;

FIG. 5 is a top plan view of the apparatus shown in FIG. 3, relative to a unique grouping of anatomical features, and according to one embodiment of the present disclosure;

FIG. 6 is a perspective view of the apparatus and unique grouping of anatomical features shown in FIG. 5;

FIG. 7 is another perspective view of the apparatus shown in FIG. 3 demonstrating the customized patient-matching surfaces of the apparatus;

FIG. 8 is a perspective view of an apparatus according to an alternative embodiment of the present disclosure;

FIG. 9 is a perspective view of an apparatus according to yet another alternative embodiment of the present disclosure.

FIG. 10 is another perspective view of the apparatus shown in FIG. 3 along with a custom fabricated instrument for use during a particular surgical procedure;

Figure 11A:
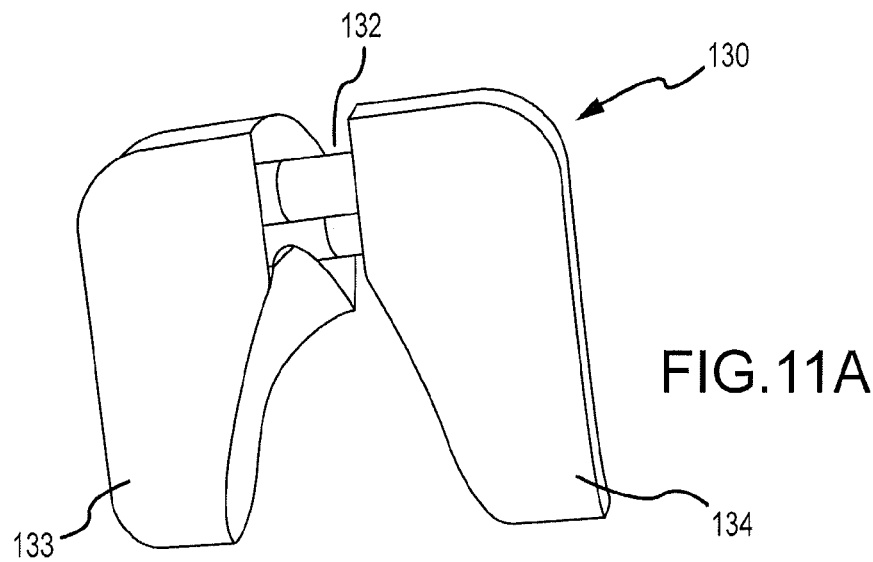
Figure 11B:
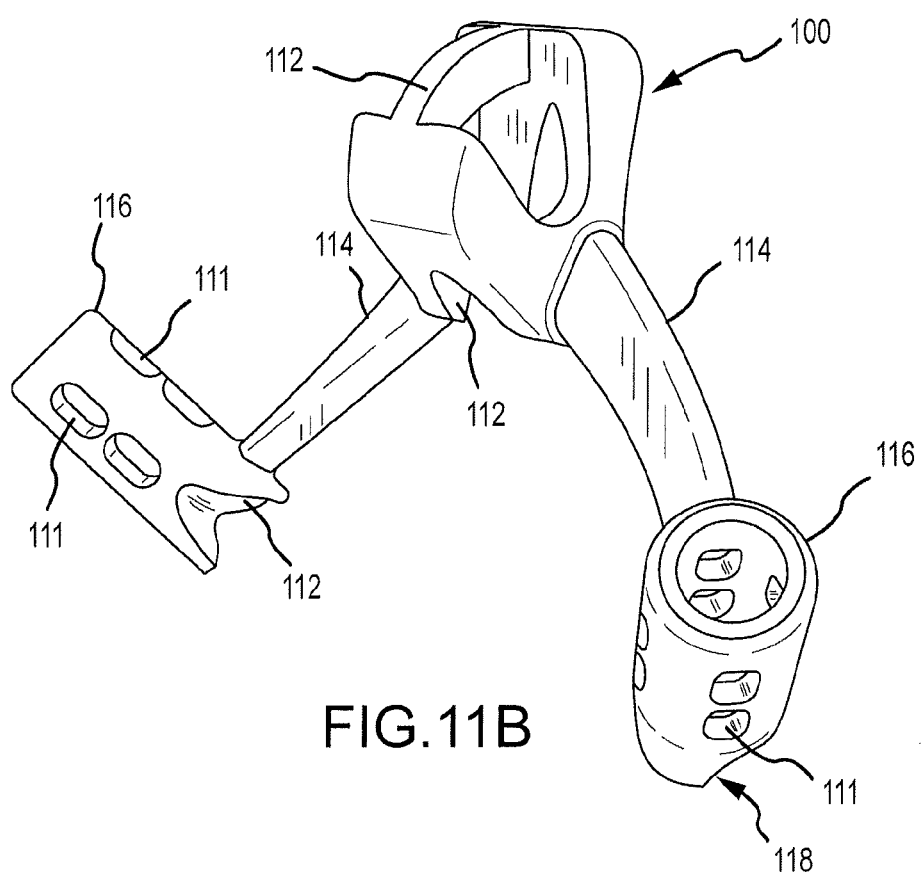
Figure 12:
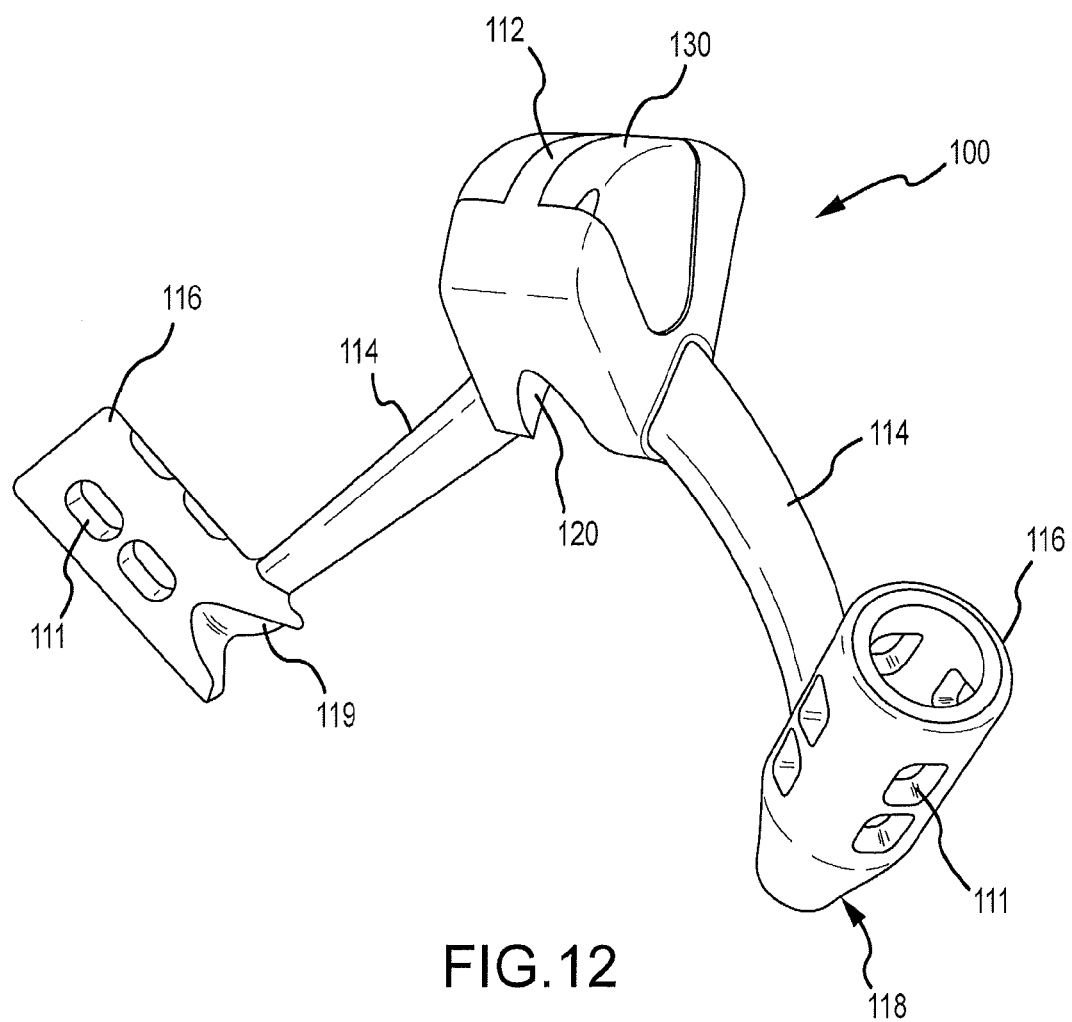
Figure 13:
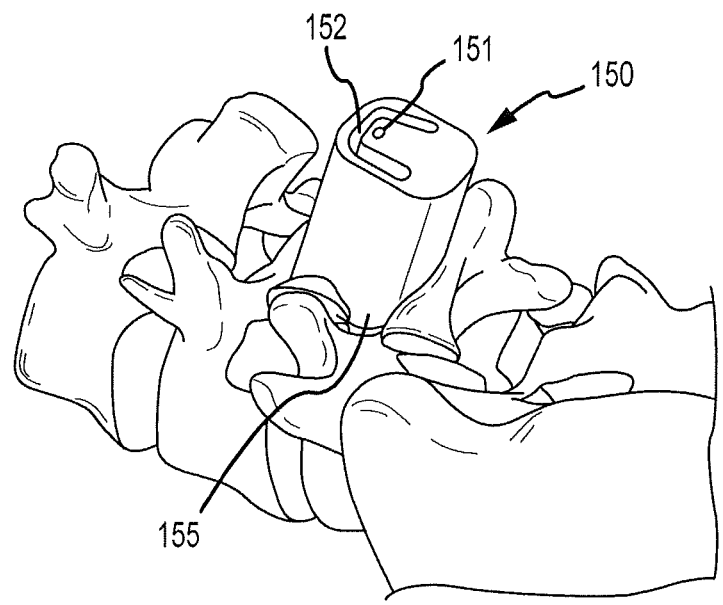
Figure 14:
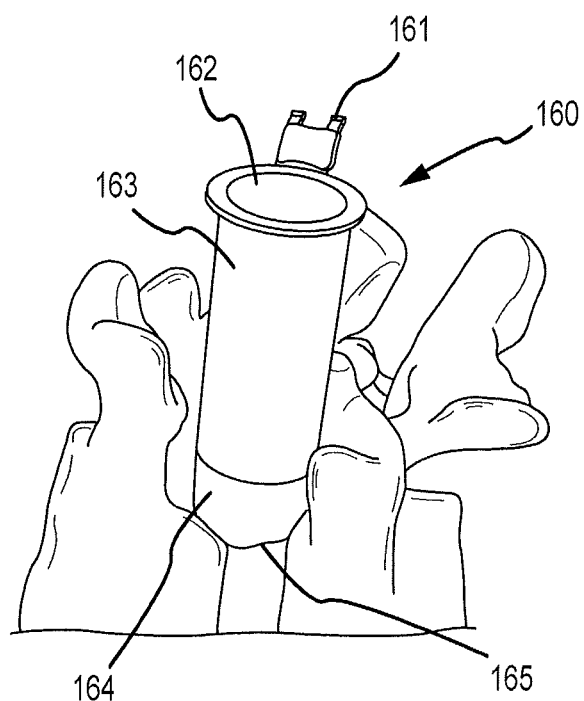
Figure 15:
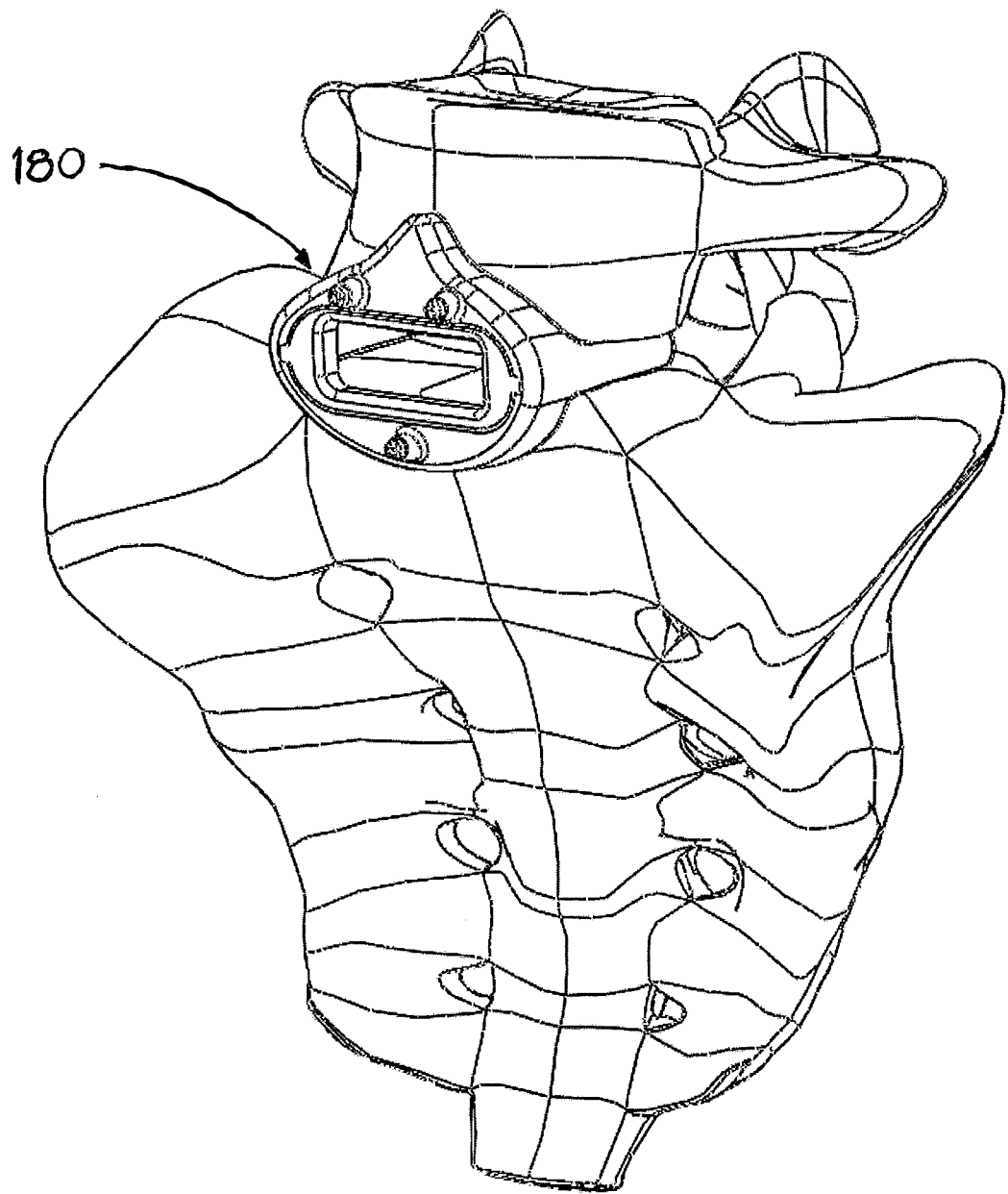
Figure 16:
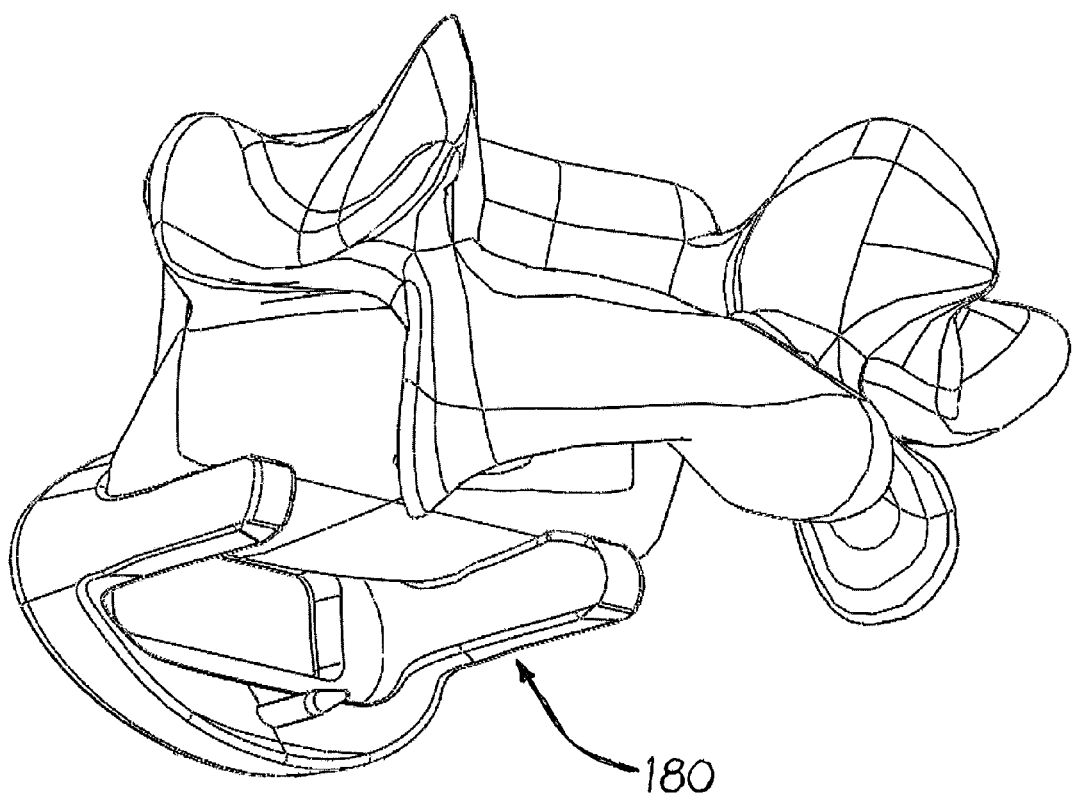
Figure 17:
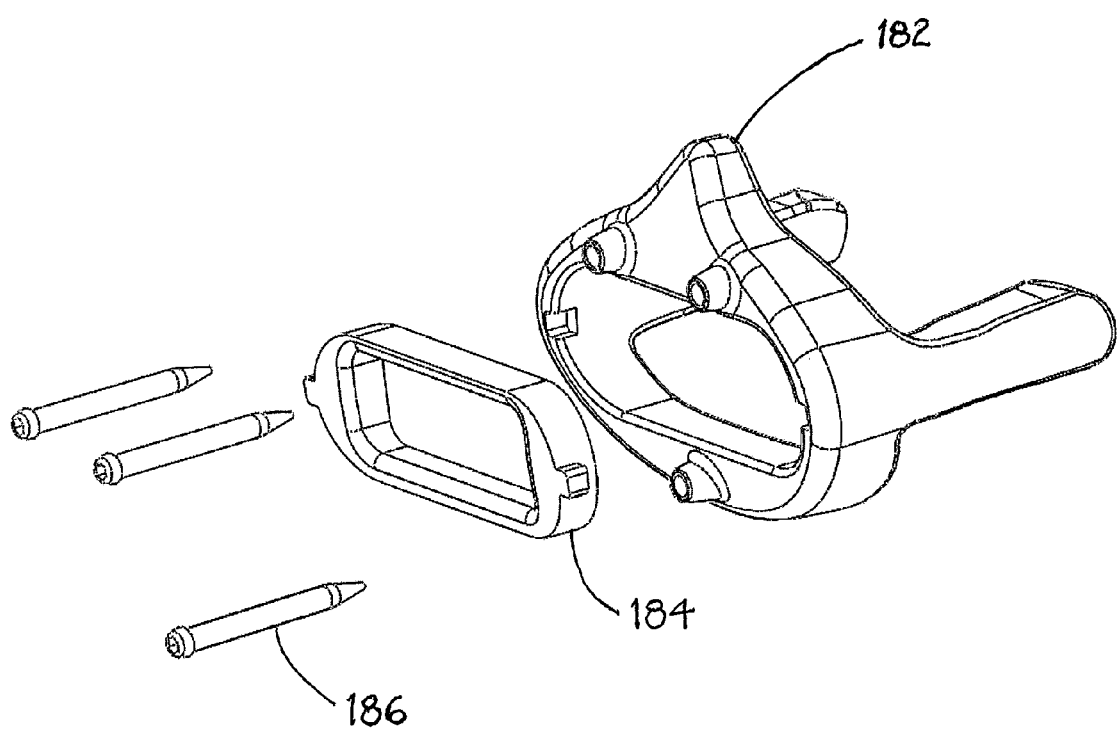

FIGS. 11A-B are perspective views of an apparatus according to another alternative embodiment of the present disclosure;

FIG. 12 is a perspective view of the apparatus shown in FIGS. 11A-B in an assembled state;

FIG. 13 is a perspective view of an apparatus according to yet another alternative embodiment of the present disclosure;

FIG. 14 is a perspective view of an apparatus according to yet another alternative embodiment of the present disclosure;

FIG. 15 is a perspective view according to yet another alternative embodiment of the present disclosure;

FIG. 16 is a different perspective view of the apparatus shown in FIG. 15; and FIG. 17 is an exploded perspective view of the apparatus shown in FIG. 15.

DETAILED DESCRIPTION

As shown in the appended Figures and described in further detail herein, the present disclosure relates to a novel system and method for developing a variety of customized, patient-matched apparatus for use in a diverse number of surgical procedures. The system and method uses a patient's unique morphology, which may be derived from capturing MRI data or CT data to derive one or more patient-matched apparatus, which comprise complementary surfaces to those encountered during the surgical procedure(s) as derived from a set of data points. According to various embodiments described herein, the patient-matched apparatus may further comprise desired axes and/or insertional trajectories. According to one alternate embodiment described herein, the patient-matched apparatus may be further matched with at least other apparatus used during the surgical procedure. Other features of the disclosure will become apparent after a review of the following disclosures and varying embodiments of the invention.

Figure 1:
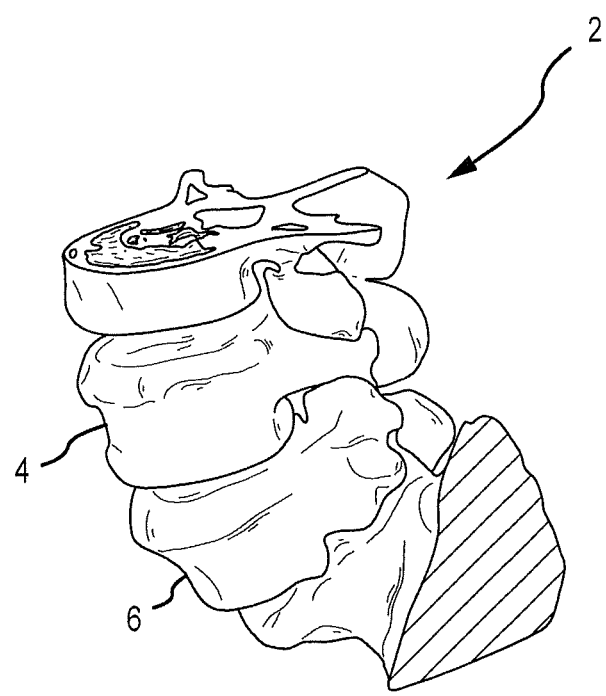

Multiple embodiments of the disclosure are depicted in FIGS. 1-17. Referring now to FIG. 1, a perspective view of a three-dimensional model of a unique grouping of anatomical features according to one embodiment of the present disclosure is shown. Here, the model 2 is comprised of multiple vertebral bodies 4, 6 but according to other embodiments may be comprised of any anatomical grouping for a particular patient. Data associated with the model 2 may be captured from a MRI or CT scan or from radiographic images of the patient's corresponding bony anatomy. The data, one captured, may be converted using known software tools to a CAD program, where the data set is representative of the model 2 and may be used to provide additional data points for forming the contours, sizes, shapes and orientations of one or more apparatus to be used in the surgical procedure.

According to an alternative embodiment, the data may be obtained from an ultrasonic or nuclear medicine scanning device. In yet another alternative embodiment, the data may be supplemented or merged with data from a bone density scanner to fabricate a device that is designed to remain in the patient after the surgical procedure is completed, or alternatively to achieve further control over the orientation of any desired axes, particularly where the surgical procedure involves insertion of one or more implantable devices. Examples of devices that remain in the patient include anchoring devices and implantable devices.

Figure 2:
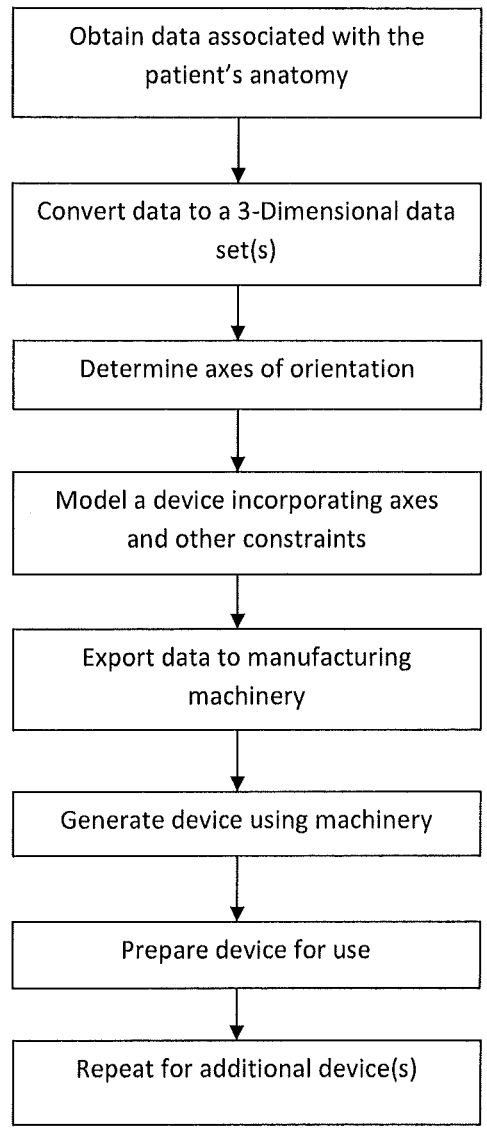

FIG. 2 is a flow chart showing the various steps of performing a method of manufacturing an apparatus, according to various embodiments described herein, for use in facilitating a surgical procedure.

The method, according to a preferred embodiment, comprises the following steps:

A) Obtaining data associated with the patient's anatomy by way of a MRI or CT scan;

B) Converting the MRI or CT scan data to a 3-Dimensional data set(s)

C) Determining one or more axes of orientation of a device to be constructed for use in facilitating the surgical procedure(s) to be performed on the patient;

D) Modeling the device for use in facilitating the surgical procedure(s) using the determined axes and accounting for any other constraints derived from the converted data set(s);

E) Generating a prototype of the modeled device by, for example, use of rapid prototyping machinery; and F) Preparing the prototype for use during the surgical procedure(s).

As shown in FIG. 2, the method may comprise additional steps or may be repeated for additional devices used in the surgical procedure.

The step of obtaining data is typically performed in a traditional manner, by subjecting the patient to a scan using MRI or CT or other suitable scanning equipment known in the art. The data is then captured by the equipment and may be converted to a 3-Dimensional data set(s) by software or other algorithmic means known in the art, such as by exporting the data into a known modeling software program that allows data to be represented, for example, in CAD format. Once this data is converted, a device may be modeled to complement the data set(s) and oriented by one or more axes determined by the surgeon either before or through observation of the data set(s) from the initial scan of the patient's anatomy.

The method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc. The prototype may be generated using known rapid prototyping machinery, or alternatively by milling machinery such as a CNC milling machine. Alternatively, the initial device fabricated by this method may be in a temporary state for further consideration and or manipulation by the surgeon, and then finally constructed using one of the methodologies described herein. The steps may be repeated for complementary devices, some or all of which may include further matching surfaces for the patient's anatomy or to the previously fabricated devices (i.e., the devices fabricated may have matching surfaces for adjoining together one or more devices, as described in greater detail below).

Alternatively, the system and method described herein may facilitate the alignment of various anatomical features for a particular patient, such as, for example, multiple vertebral bodies in a patient to correct spinal deformities. For example, the data set(s) may provide an initial location for the anatomical features, but may be further manipulated by the surgeon in a pre-operative setting to create a desired data set(s), such as a final location for the anatomical features once the surgical procedure(s) are completed. In this manner, the devices formed by the system and method described above may be used in either an initial location or a final location for the anatomical features, and be matched to those specific locations and orientations for each stage of the surgical procedure. These staged devices would in turn provide the surgeon with a visual guide to determine the degree of correction achieved through the surgical procedure, as compared to the pre-operative plan. Other variations on the method of the present disclosure are described in the Summary of the Invention and included in the appended claims.

Fabrication methods may comprise the use of a rapid prototyping machine, such as a stereolithography machine or a fused deposition modeling machine. One example of such a rapid prototyping machine is commercially available from 3D Systems and known as Model SLA-250/50. The rapid prototyping machine selectively hardens a liquid or other non-hardened resin into a three-dimensional structure, which can be separated from the remaining non-hardened resin, washed/sterilized and used directly as the apparatus. The prototyping machine receives the individual digital data sets and produces one structure corresponding to each of the desired apparatus.

Generally, because stereolithographic machinery produces a resin, which may have less than optimal mechanical properties (which may not be generally acceptable for a particular surgical use), the prototyping machine may alternatively be used to produce a mold. After the model is prepared, a conventional pressure or vacuum molding machine may be used to produce the apparatus from a more suitable material, such as stainless steel, titanium alloy, aluminum alloy, chromium alloy, PEEK, carbon fiber, or other metals or metal alloys.

According to another alternative embodiment, the system and method may comprise providing the data set(s) to a CNC machine, which in turn may be utilized to manufacture a custom milled apparatus from one of the more mechanically sound materials listed above. In yet another alternative embodiment, volume manufacturing of apparatus in accordance with the embodiments described herein may also be achieved, for example, where a particular orientation or insertion trajectory is common among a large grouping of patients.

According to one particular embodiment of the present disclosure, a system and method is provided for fabricating apparatus for use with a variety of surgical procedures associated with a patient's spine. Individuals who suffer degenerative disc disease, natural spine deformations, a herniated disc, spine injuries or other spine disorders often require surgery on the affected region to relieve the individual from pain and prevent further injury. Such spinal surgeries may involve removal of damaged joint tissue, insertion of a tissue implant and/or fixation of two or more adjacent vertebral bodies, with the surgical procedure varying depending on the nature and extent of the injury.

For patients with varying degrees of degenerative disc disease and/or nerve compression with associated lower back pain, spinal fusion surgery, or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra.

Fusion may occur in the lumbar, interbody or cervical spine region of a patient. Fusion requires tools for accessing the vertebrae and implanting the desired implant, any bioactive material, etc. Such procedures often require introduction of additional tools and/or instruments, including drills, drill guides, debridement tools, irrigation devices, vises, clamps, cannulae, retractors, distracters, cutting tools, cutting guides and other insertion/retraction tools and instruments. The insertion, alignment and placement of these tools, instruments and fixation devices are critical to the success of the operation. As such, providing a customized and patient-specific tool or instrument increases the likelihood that the surgical procedure will be successful.

Figure 3:
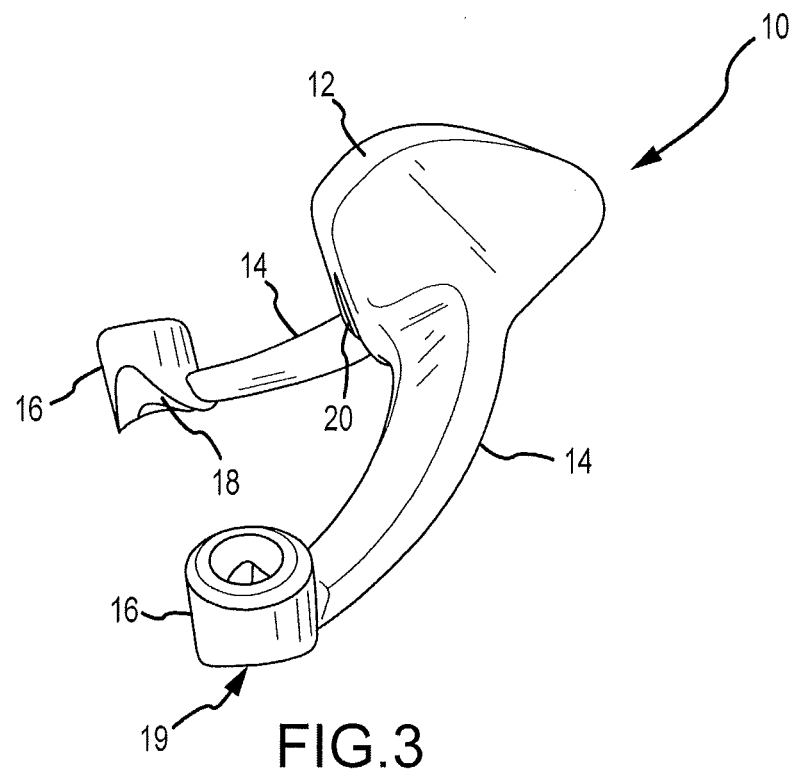
Figure 4:
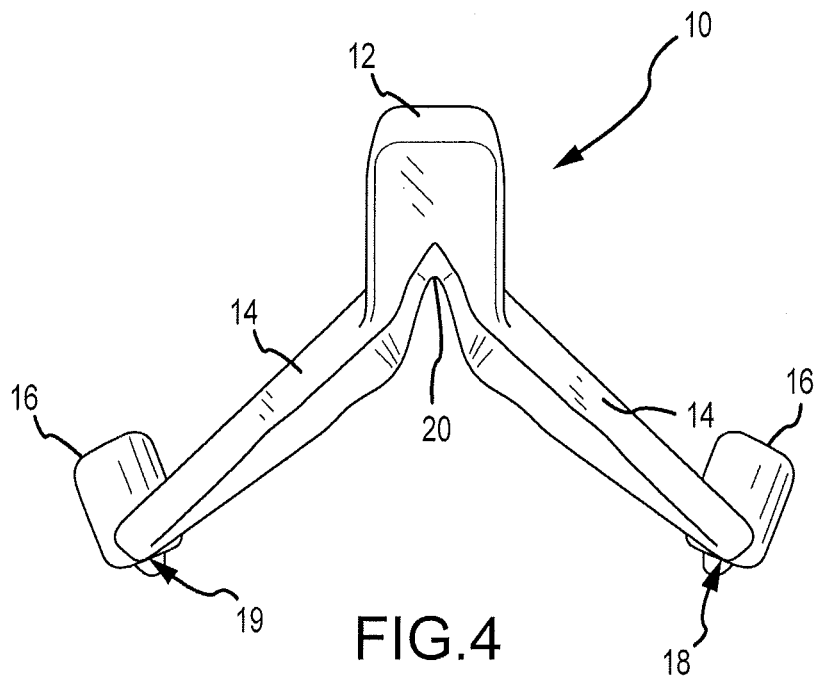

For example, one particular apparatus formed by the system and method described above and that may be used for a particular fixation related surgery is depicted in FIGS. 3 and 4. According to one embodiment of the present disclosure, the apparatus may be in the form of a pedicle screw guide 10, which is comprised of a medial body 12 and two generally elongated wings 14, each wing 14 terminating in a generally cylindrical column 16. In a preferred embodiment each of the cylindrical columns 16 is substantially hollow to permit one or more types of devices to be inserted therethrough, as depicted in FIG. 3. The medial body 12 further comprises a longitudinal cavity 20 formed about a lower surface of the medial body 12 (shown from the perspective view taken in FIG. 3). Each of the cylindrical columns 16 further comprise a lower, patient-contacting surface 18, 19, which in conjunction with the longitudinal cavity 20 provide a plurality of patient specific contours for matching with a plurality of anatomical features, as described in greater detail below.

The contours and locations of the lower, patient-contacting surfaces 18, 19 and the longitudinal cavity 20 are formed by use of data set(s) converted from a MRI or CT scan of the patient. The remainder of the pedicle screw guide 10 shown in FIGS. 3 and 4 may be formed to meet the surgeon's particular preferences. For example, the wings 14 need only be of sufficiently length to locate the two cylindrical columns 16 in the location of the corresponding patient-matched anatomical features. The wings may take on other shapes, orientations, thicknesses, etc. without deviating from the novel aspects of this disclosure. Similarly, the medial body 12 need only be sized to accommodate the longitudinal cavity 20, and may comprise other extensions other than the wings 14 to aid in grasping or manipulating the pedicle screw guide 10 as desired.

Additionally, the wings 14 may be made from a semi-malleable or semi-rigid material to create at least a partial interference fit when the pedicle screw guide 10 is placed on the corresponding anatomical grouping for the particular surgery. For example, a snap or interference fit may be formed by subtle deflection of the wings 14 when placing the two cylindrical columns 16 adjacent the inferior articular process, and then deflect to the desired location once the wings are positioned in their final orientation. Further aspects of the disclosure in this respect are described in greater detail below.

Figure 5:
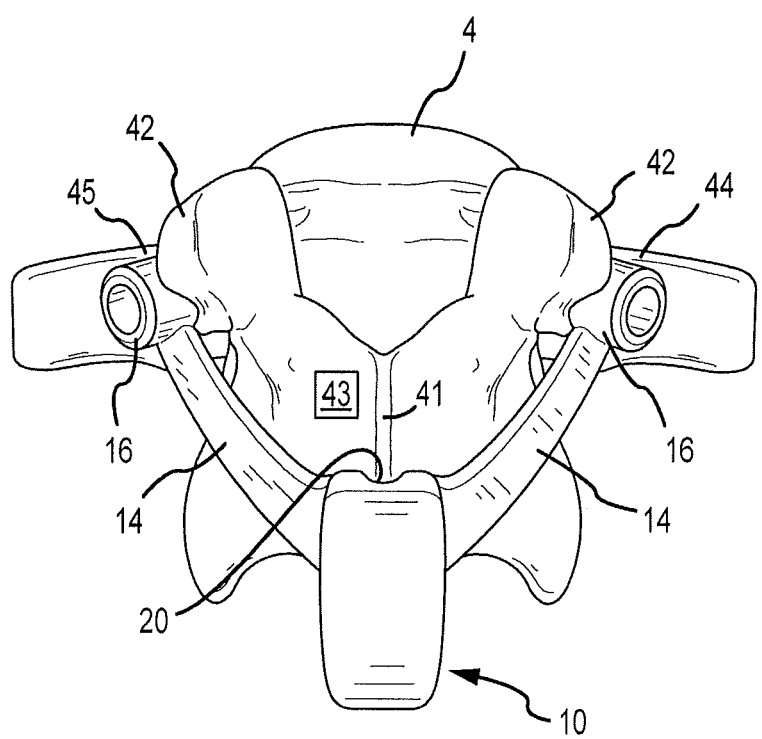

FIG. 5 is a plan view of the apparatus shown in FIG. 3 relative to a unique grouping of anatomical features according to one embodiment of the present disclosure. Here, the pedicle screw guide 10 is positioned so that the medial body 12 is centrally located above the central portion of a vertebral body 4, such that the longitudinal cavity 20 mates with the contours of the spinous process 41 for this particular vertebral body 4. Similarly, the cylindrical columns 16 are positioned one at each medial side of the pedicle screw guide 10 so that the wings 14 span the lamina 43 of the vertebral body 4 and the cylindrical columns 16 are located proximate to the inferior articular process 44, 45. The lower, patient-contacting surface 18, 19 of cylindrical columns 16 are formed to mate with the contours of the inferior articular process 44, 45 and behind the superior articular process 42.

Thus, the pedicle screw guide 10 provides a plurality of mating or matching locations, any one of which, if not positioned correctly, will impact the seating of the other two. In this aspect the pedicle screw guide provides a notable improvement over the prior art, which may be slightly rotated, misaligned or misplaced and still appear to the surgeon as if the device is properly seated. The redundancy and plurality of mating surfaces ensures that the pedicle screw guide 10 is both properly located and properly aligned. If the pedicle screw guide 10 is not properly located or aligned, the lower, patient-contacting surfaces 18, 19 will not fit on each of the inferior articular process 44, 45 and still permit the longitudinal cavity 20 to be firmly seated on the spinous process.

Figure 6:
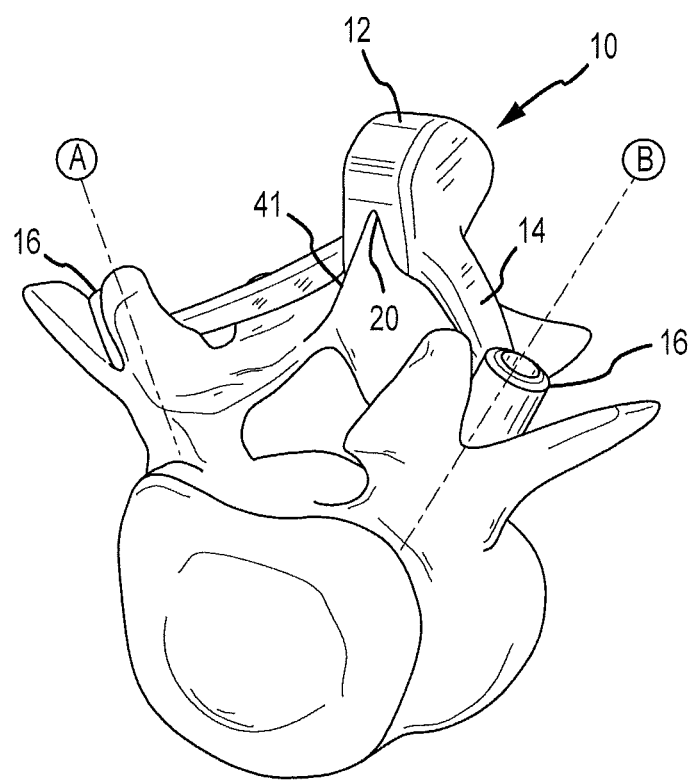

FIG. 6 is a perspective view of the apparatus shown in FIG. 5. Desired insertion trajectory lines A, B are shown to demonstrate that the locating of the cylindrical columns 16 is in addition to the orientation of the axes for each of the cylindrical columns 16, which may be independent relative to their seating adjacent the inferior articular process 44, 45 (i.e., the direction of the axis relative to normal may be different among the cylindrical columns 16). The orientation of the cylindrical columns 16 is also derived from the data set(s) described above, and in one preferred embodiment is selected based on the orientation that will permit a fixation device (i.e., pedicle screw) to be inserted consistent with the location of the pedicle and in a direction that avoids penetration of the fixation device from the pedicle (i.e., eliminates the possibility of the screw either extending through the pedicle or becoming inserted at an angle that causes the pedicle screw to exit the side of the pedicle).

Figure 7:
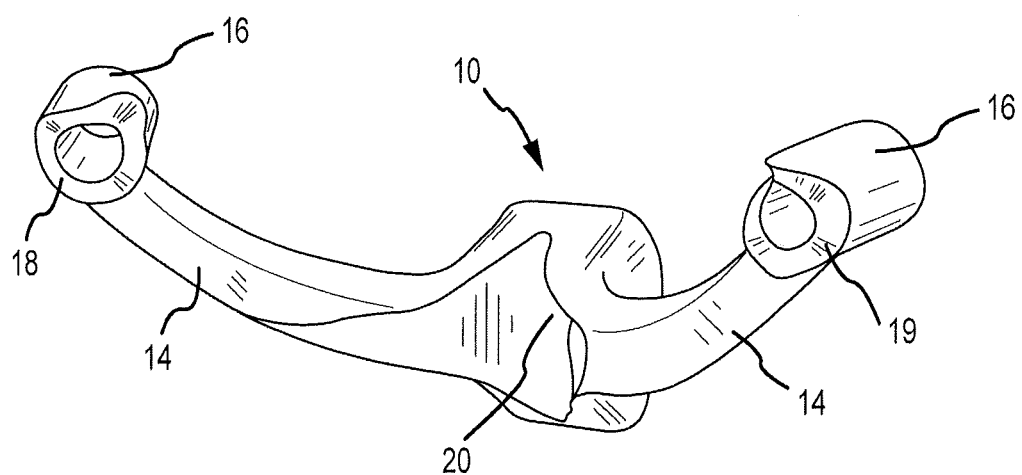

The customized or configured patient-contacting surfaces of the apparatus shown in FIGS. 3-6 are demonstrated by the bottom perspective view of the pedicle screw guide 10 in FIG. 7. Here, the lower, patient-contacting surfaces 18, 19 may comprise dynamic contours having multiple compound radii, such that the surfaces 18, 19 are completely congruent with the corresponding anatomical features of the vertebrae. Thus, the surfaces conform substantially to the surface of the vertebrae where the cylindrical columns 16 are to be located during the surgical procedure, and would not conform substantially to a different surface of the vertebrae. In this manner, the surgeon is informed immediately if the pedicel screw guide 10 is misaligned, because it will not properly seat on the vertebrae.

Figure 8:
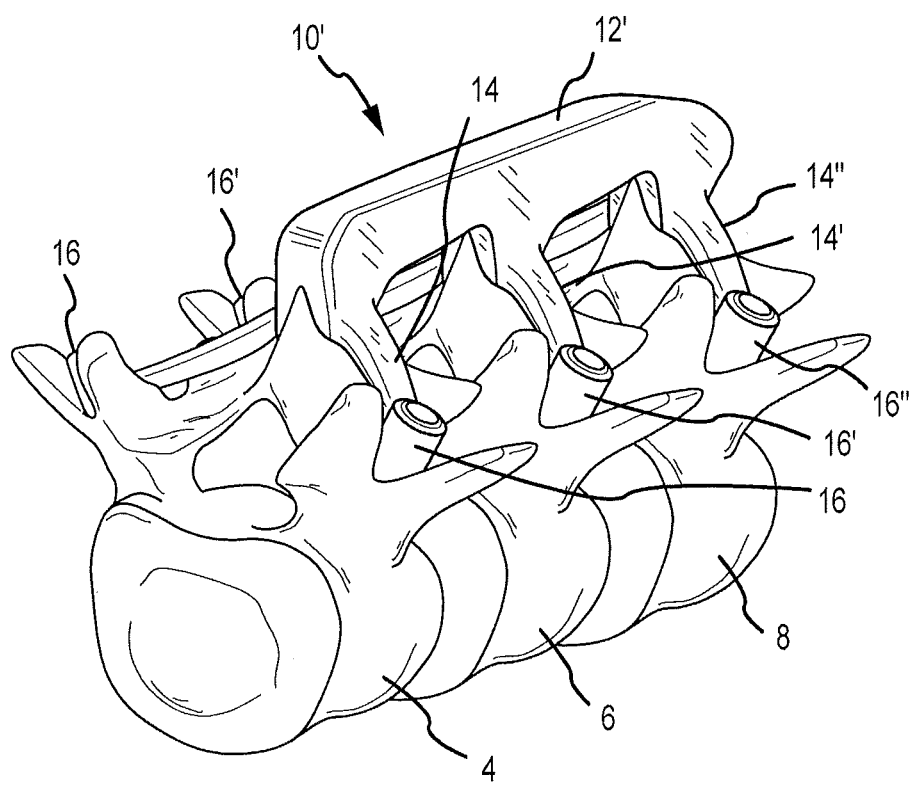

FIG. 8 shows an apparatus according to an alternative embodiment of the present disclosure. In this embodiment, a multi-level pedicle screw guide 10' is shown relative to several adjoining vertebral bodies 4, 6, 8. The multi-level pedicle screw guide 10' comprises multiple secondary wings 14' and tertiary wings 14", which each have corresponding cylindrical columns 16', 16" for inserting and aligning a plurality of pedicle screws into the adjoining vertebral sections 6, 8. It is expressly understood that multiple levels in number greater than or less than three may be achieved without departing from the spirit of the present invention.

Figure 9:
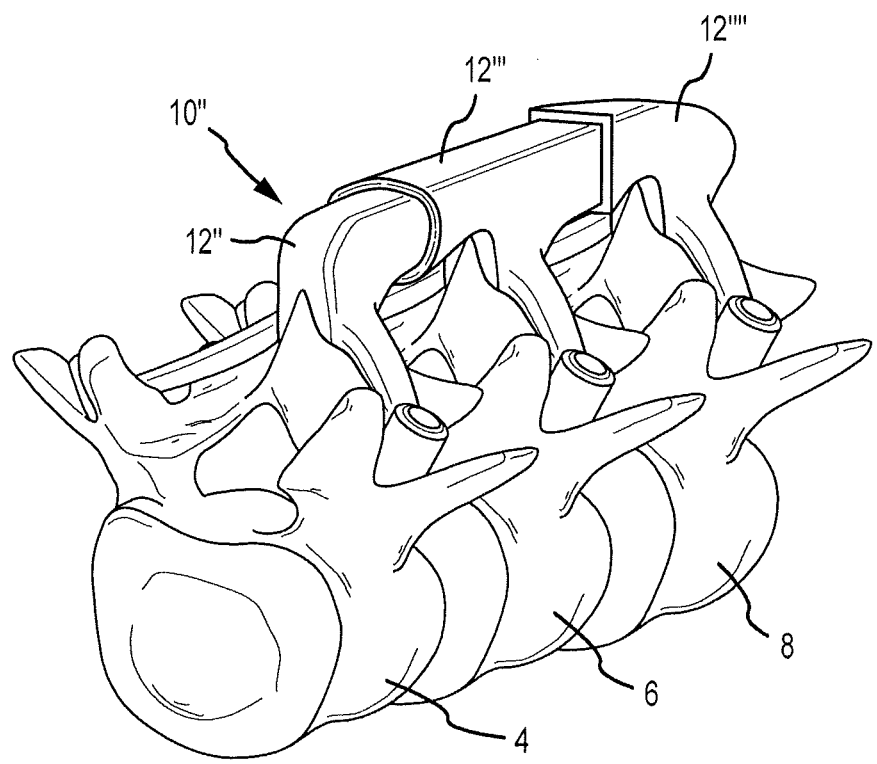

FIG. 9 shows an apparatus according to yet another alternative embodiment of the present disclosure, which is comprised of multiple sections 12", 12''', 12''''. Similar to the embodiment shown in FIG. 8, this pedicle screw guide 10''' permits alignment and insertion of pedicle screws in multiple levels 4, 6, 8 of the spine. However, the multiple sections 12", 12'", 12"" each have a modified medial body that comprises an engaging end and a receiving end, such that the multiple sections 12", 12'", 12"" may be joined as shown in FIG. 9. The receiving and engaging ends of each of the multiple sections 12", 12'", 12"" are different so that when assembled, only the proper ordering of the sections 12", 12'", 12"" may be achieved (i.e., section 12" may only be joined with section 12'"). This figure demonstrates yet another aspect of the present disclosure, in particular, the ability to mate or join specific devices adjacent to one another to further ensure alignment and mating with the particular anatomical features associated with each device.

Figure 10:
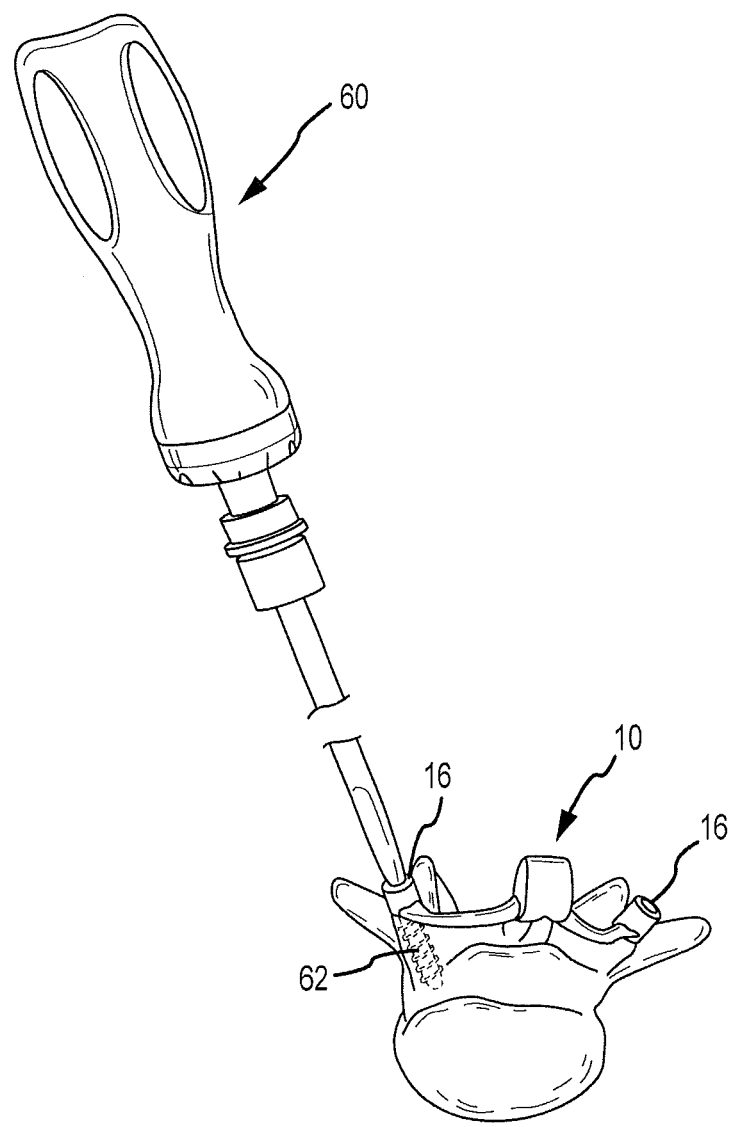

FIG. 10 shows an apparatus according to the embodiment of FIG. 5 with a customized instrument, which may be used in concert with the apparatus during a particular surgical procedure. For example, during a spinal fusion procedure such as the one described above, it is common for the surgeon to attach one or more pedicle screws to the vertebrae of the patient to achieve the desired fusion of intra-vertebral bodies. The cylindrical column 16 may have a internal diameter that corresponds with a gradually increasing external diameter of the instrument 60 such that the instrument 60 may only be advanced into the cylindrical column 16 to a predetermined distance, thereby providing a hard stop and in turn providing means for preventing the pedicle screw 62 from advancing too far into the bony anatomy of the patient. According to yet another embodiment, the hollow portion of the cylindrical column 16 may have a section with a narrower internal diameter (not shown in FIG. 10), which corresponds to a end-stop fitted to the external diameter of the instrument 60 in a manner and location to prevent the instrument from over penetrating the cylindrical column 16 and thereby inserting the pedicle screw 62 beyond a safe limit.

FIG. 11 is a perspective view of an apparatus according to yet another alternative embodiment of the present disclosure. Here, the apparatus is a pedicle screw guide 100 which further comprises a narrow bridge 112 about the medial body, which permits a collar 130 to be coupled with the modified pedicle screw guide 100, as shown in FIG. 12. The collar 130 may comprise a contoured lower surface matching the spinous process of the patient (similar to the longitudinal cavity of the embodiment shown in FIG. 3), and may be inserted into the pedicle screw guide 100 for matching the particular anatomical feature for the vertebrae operated on during the surgery. Thus, in this embodiment, the collar 130, in addition to the lower patient-contacting surfaces 118, 119 of the two cylindrical columns 116, comprises at least one of the patient-matching contours, and may be removed and replaced with other collars of differing contour as required for surgical procedures on different vertebrae. In this embodiment, the cylindrical columns 116 may further comprise one or more apertures 111 to facilitate visualization of the pedicle screw while it is being advanced into the cylindrical columns 116.

FIG. 13 is a perspective view of an apparatus for facilitating a surgical procedure according to yet another alternative embodiment of the present disclosure. In this embodiment, the apparatus formed by the system and method described above is comprised of a laminectomy cutting guide 150. This laminectomy cutting guide further comprises at least one alignment channel 151 for inserting a guide wire or other securing element, and a cutting slot 152 for directing the path of a blade or other cutting edge. As with the pedicle screw guide described in FIG. 3 above, this laminectomy cutting guide 150 also comprises a lower patient-contacting surface 155 which permits the laminectomy cutting guide 150 to mate with one or more vertebral bodies. Although shown in FIG. 13 as a generally rectangular prism, it is expressly understood that other geometrical shapes for the laminectomy cutting guide 150 are equally as practical, and considered within the scope of the disclosure.

FIG. 14 shows yet another alternative embodiment of the present disclosure. In this embodiment the apparatus formed by the system and method described above is comprised of a tube retractor 160, which also comprises a lower patient-contacting surface 165. This patient-contacting surface 165 may be formed in a section 164 of the tube retractor that is selectively removable from the cylindrical body 163 of the tube retractor 165, such that the tube retractor 165 may be reused in a number of surgeries while the section 164 is reformed and coupled to the cylindrical body 163 for each patient. The tube retractor also comprises a generally hollow inner lumen 162 and at least one tab 161 for manipulating during insertion and that assists the surgeon in ensuring proper alignment of the tube retractor 160.

FIGS. 15-17 demonstrate yet another alternative embodiment of the present disclosure. In this embodiment, the template may comprise a patient-matched guide 180 for facilitating the placement of one or more interbody devices, such as by way of example but not limitation, an implantable cage for introducing one or more bioactive substances or bone graft, or an artificial disc. In FIGS. 15 and 16, the patient-matched guide 180 is shown in one potential location relative to a unique anatomical grouping (between two adjacent vertebrae) for assisting the surgeon for placing one or more interbody devices.

In FIG. 17, the patient-matched guide 180 is shown in an exploded view to demonstrate how a plurality of components may be fabricated using the system and method described above for a particular surgical procedure. These components include a patient-specific insert 182, a guide sleeve 184 and connectors 186, which in a finally assembled state form the patient-matched guide 180 shown in FIG. 15.

The apparatus disclosed herein may be made of a variety of different materials. These materials may include, by way of example but not limitation, stainless steel, titanium alloy, aluminum alloy, chromium alloy, and other metals or metal alloys. These materials may also include, for example, PEEK, carbon fiber, ABS plastic, polyurethane, resins, particularly fiber-encased resinous materials rubber, latex, synthetic rubber, synthetic materials, polymers, and natural materials.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials in appended Exhibit A hereto are expressly made a part of this disclosure and incorporated by reference herein in their entirety.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A patient specific pedicle screw guide that anatomically mates with the spinous processes of a particular vertebral body, comprising:
   a medial body comprising a longitudinal cavity located on a first lower surface of the medial body, such that the longitudinal cavity provides a first patient-contacting surface that mates with at least one contour of a first spinous process;
   a first elongated wing extending laterally from a first side of the medial body and terminating with a first cylindrical column, wherein the first cylindrical column comprises a second lower surface comprising a second patient-contacting surface that mates with at least one contour of a second spinous process; and
   a second elongated wing extending laterally from a second side of the medial body and terminating with a second cylindrical column, wherein the second cylindrical column comprises a third lower surface comprising a third patient-contacting surface that mates with at least one contour of a third spinous process.

2. The patient specific pedicle screw guide of claim 1, wherein the first cylindrical column and the second cylindrical column are substantially hollow.

3. The patient specific pedicle screw guide of claim 1, wherein the first cylindrical column and the second cylindrical column further comprise a narrower internal diameter, forming a first end-stop and a second end-stop to prevent an instrument from over penetrating a pedicle screw beyond a safe limit.

4. The patient specific pedicle screw guide of claim 2, wherein the first elongated wing and the second elongated wing comprise a deflection, that provides an interference fit when positioning the pedicle screw guide in a final orientation wherein the patient-contacting surfaces mate with the spinous processes.

5. The patient specific pedicle screw guide of claim 2, wherein the first and second cylindrical columns both further comprise one or more apertures.

6. A patient specific pedicle screw guide system comprising at least two of the pedicle screw guides of claim 1, wherein the at least two pedicle screw guides are linked together along the longitudinal axis.

7. The patient specific pedicle screw guide of claim 1 wherein at least one of the first cylindrical column and the second cylindrical column comprises a bore and is configured to receive at least one device in the bore.

8. The patient specific pedicle screw guide of claim 7 wherein the at least one device is selected from the group consisting of a bone anchor, an implant, a drill, a rasp, a blade, a screwdriver, a curette, a retractor, a distractor, an elevator and a debridement instrument.

9. The patient specific pedicle screw guide of claim 1 wherein the guide is formed by a rapid prototyping machine.

10. The patient specific pedicle screw guide of claim 1 wherein the guide is comprised of a material selected from the group consisting of a stainless steel, a titanium alloy, an aluminum alloy, a chromium alloy, a PEEK material, a carbon fiber, an ABS plastic, a polyurethane, a resin, a fiber-encased resinous material, a rubber, a latex, a synthetic rubber, a polymer, and a natural material.

11. The patient specific pedicle screw guide of claim 1, wherein the patient specific pedicle screw guide is manufactured to incorporate at least one unique data set from the group consisting of a computed tomography device, a magnetic resonance imaging device, an ultrasound device, a radiographic image, and a nuclear medicine scanning device.

12. The patient specific pedicle screw guide of claim 1, further comprising one or more axes of orientation of the patient specific pedicle screw guide, wherein the axes correlate to defined pathways through the patient specific pedicle screw guide, which are operatively associated with at least one device, tool, instrument or implant, and which permit the at least one device, tool, instrument or implant to be inserted in the defined pathways.

13. The patient specific pedicle screw guide of claim 12, further comprising at least one attachment or insert which may be selectively coupled to the patient specific pedicle screw guide for aligning the at least one device, tool, instrument or implant, and which may be removed from the patient specific pedicle screw guide after a single use or multiple uses.

14. The patient specific pedicle screw guide of claim 1, further comprising a bridging element for joining the patient specific pedicle screw guide with one or more other patient specific pedicle screw guides, which facilitates alignment and orientation of the plurality of joined patient specific pedicle screw guides with the associated patient anatomy.

15. The patient specific pedicle screw guide of claim 12, wherein the one or patient specific pedicle screw guide comprises a hard stop for preventing the at least one device, tool, instrument or implant from advancing too far into an anatomical feature of a patient.

16. The patient specific pedicle screw guide of claim 14, wherein at least two patient specific pedicle screw guides are configured to be aligned along a longitudinal axis of a human spine.

17. The patient specific pedicle screw guide of claim 1 further comprising a selectively removable collar, wherein the collar comprises at least one independent patient-contacting surface formed to be substantially congruent with a corresponding anatomical feature of a patient.

18. The patient specific pedicle screw guide of claim 1, further comprising first and second patient-specific bores passing through the corresponding first and second cylindrical columns and having patient specific-orientations for guiding at least one fixation element into corresponding first and second anatomic portions of a patient.

19. The patient specific pedicle screw guide of claim 1, wherein in the second and third patient-contacting surfaces further comprise portions configured to mate with corresponding first and second transverse processes of a vertebra of a patient.

20. The patient specific pedicle screw guide of claim 1, further comprising an arcuate bridge, the arcuate bridge comprising at least one surface configured to permit a user to apply pressure and transmit forces through the arcuate bridge to the first and second elongated wings.

* * * * *